US006180718B1

(12) United States Patent
Boehm et al.

(10) Patent No.: US 6,180,718 B1
(45) Date of Patent: Jan. 30, 2001

(54) PROCESS FOR PREPARATION OF AROMATIC AND HETEROAROMATIC MOLECULES

(75) Inventors: Terri L. Boehm; John C. Hodges; Howard D. H. Showalter, all of Ann Arbor, MI (US)

(73) Assignee: Warner-Lambert Company, Ann Arbor, MI (US)

(*) Notice: Under 35 U.S.C. 154(b), the term of this patent shall be extended for 0 days.

(21) Appl. No.: 09/125,233

(22) PCT Filed: Feb. 18, 1997

(86) PCT No.: PCT/US97/02402

§ 371 Date: Aug. 13, 1998

§ 102(e) Date: Aug. 13, 1998

(87) PCT Pub. No.: WO97/31880

PCT Pub. Date: Sep. 4, 1997

Related U.S. Application Data

(60) Provisional application No. 60/012,634, filed on Mar. 1, 1996.

(51) Int. Cl.[7] .............................. C08F 8/00; C08L 83/00
(52) U.S. Cl. ......................... 525/100; 525/105; 525/106; 436/518; 548/110; 548/118
(58) Field of Search ........................... 436/518; 548/118, 548/110; 525/100, 105, 106

(56) References Cited

FOREIGN PATENT DOCUMENTS

| 9516712 | 6/1995 | (WO) | |
|---|---|---|---|
| WO 95/16712 * | 6/1995 | (WO) | ............................... C08F/8/00 |

OTHER PUBLICATIONS

*Journal of Organic Chemistry*, vol. 60, No. 19, 1995, pp 6006–6007, A Silicon–based Linker for Traceless Solid–Phase Synthesis, M. J. Plunkett, et al.
*Journal of the Chemical Society, Chemical Communication*, No. 13, 1985, pp. 909–911, Polymer–anchored Organosilyl Protecting Group in Organic Synthesis, Tak–Hang Chan, et al.
*Journal of the American Chemical Society*, vol. 117, No. 21, 1995, pp. 5712–5719, Major Simplifications in Oligosaccharide Syntheses Arising from a Solid–Phase Based Method: An Application to the Synthesis of the Lewis b Antigen, John T. Randolph, et al.
*Chemical Abstracts*, vol. 125, No. 19, 1996, p 1118, Col. 2, Abstract No. 247505v, Development of a Novel Silyl Ether Linker for Solid–Phase Organic Synthesis, Boehm, et al.
*J. Org. Chem.*, vol. 61, 1996, pp 6498–6499, Development of a Novel Silyl Ether Linker for Solid–Phase Organic Synthesis, Boehm, et al.
Aldrich Chemical Catalogue p. 438, 1990.*
Greene and Wuts, Protective Groups in Organic Synthesis, John Wiley and Sons, New York, pp. 68–87, 1991.*
Randolph et al., Major Simplifications . . . , J. Am. Chem. Soc., v.117, p. 5712–5719, May 31, 1995.*
Routledge et al., A new Deprotection . . . , Bioorganic and Med. Chem. Letters, v5, No. 18, p. 2059–2064, Sep. 21, 1995.*
Wessel et al., Tris(dimethylamino) . . . , Angew. Chem. Int. Ed. Engl., v.34, No. 4, p. 443–445, Feb. 1, 1995.*
Salmoto et al., A mild Procedure for . . . , Tetrahedron Letters, v.27, No. 14, p. 1607–1610, 1986.*
Couret et al., Le (chlorodiisopropyl)silyl . . . , Journal of Organometallic Hemistry, v.440, p. 223–242, 1992.*
Gallop et al., Applications of Combinatorial . . . , Jounral of Medicinal Chemistry, v.37, No. 9, p. 1233–1251, 1994.*

* cited by examiner

*Primary Examiner*—Bennett Celsa
(74) *Attorney, Agent, or Firm*—Merchant & Gould P.C.

(57) ABSTRACT

A process for the attachment of aromatic or heteroaromatic rings to a polymeric support via a silyl ether linkage is described. Such process involves the synthesis of a chlorodialkyl aryl or heteroarylsilane which is then coupled to a polymeric support via a hydroxyl functionality to form a polymer-bound silyl ether. Further modification provides a polymer-bound small organic molecule that is cleaved from the polymeric support under mild conditions to give an aryl or heteroaryl silanol or a compound in which the aryl or heteroaryl carbon-silicon bond is replaced with a carbon-hydrogen, carbon-halogen, carbon-hydroxyl, carbon-sulfur, or carbon—carbon bond. Such methods are useful for the preparation of a library of diverse aromatic and heteroaromatic compounds by both manual and automated synthesis.

27 Claims, No Drawings

PROCESS FOR PREPARATION OF AROMATIC AND HETEROAROMATIC MOLECULES

This is a national stage of PCT/US97/02402 filed Feb. 18, 1997, which claims the benefit of Provisional Application Ser. No. 60/012,634 filed Mar. 1, 1996.

TECHNICAL FIELD

This invention pertains to processes in solid-supported organic synthesis which have utility in the construction of libraries of molecules bearing aromatic or heteroaromatic functionality that are to be screened for biological activities which would render them useful as pharmaceuticals or agrochemicals. More specifically, it pertains to the use of aryl- and heteroaryl-silyl ethers in linking synthetic intermediates to a solid-support during an organic synthesis, methods for attaching starting materials and methods for cleaving final products.

BACKGROUND OF THE INVENTION

Combinatorial chemistry and automated organic synthesis have proven to be highly effective means for the generation of multiplicities of novel molecules known as libraries. As the size of such a library grows, so does the likelihood that it will contain individual molecules with useful biological activities which may be employed in the treatment of human, animal, and plant diseases.

One strategy for increasing the speed at which novel libraries can be generated is to attach a synthetic starting material, also known as a synthon, to a solid-support. Subsequent synthetic transformations are carried out on the solid-supported synthon to elaborate it into the molecules of interest which are either tested for biological activity while still attached to the support or cleaved from the support prior to biological evaluation. Efficiency is introduced into the syntheses relative to traditional solution methods because tedious and time consuming purifications at each intermediate synthetic step are reduced to a simple filtration and rinsing of the polymer supported intermediate. Solid-supported methodologies, combined with automation can dramatically increase the rate at which a library of synthetic molecules may be prepared. While the disciplines of solid-supported peptide and nucleic acid chemistry are well known and have been widely practiced, the solid-supported synthesis of small organic molecules with pharmaceutical and agrochemical utility is a burgeoning science.

Since an overwhelming majority of pharmaceutical and agrochemical agents bear at least one aromatic or heteroaromatic ring, flexible processes for attachment of aromatic and heteroaromatic synthons to solid supports have tremendous value to those interested in generating libraries of molecules with pertinent biological activities. Cleavage of carbon-silicon bonds by ipso-desilylation is a strategy by which an aromatic or heteroaromatic ring may be cleaved from a silicon ether linkage to a polymeric support. A major advantage of this method is that it is possible to have no trace of the linker remain in the target molecule, unlike the amide and ester linkages commonly used in solid-supported peptide chemistry, which leave a portion of the linker functionality, typically acid, ester, amide, amine or phenol behind. Proto-ipsodesilylations will provide pharmaceuticals and agrochemicals in which the carbon-silicon bond is replaced with a carbon-hydrogen bond. By using other ipso-desilylation reactions, it is also possible to incorporate desirable functionality which is unrelated to the linker by replacing the carbon-silicon bond with carbon-oxygen, carbon-sulfur, carbon—carbon or carbon-halogen bonds in the course of cleavage from the solid-support.

WO 95/16712 describes silicon-based polymer resins and silane linkers, methods for their preparation and their use in the synthesis of libraries of aromatic carbocycles to be screened as pharmaceutical agents. Plunkett and Ellman describe "A Silicon-Based Linker for Traceless Solid-Phase Synthesis in *The Journal of organic Chemistry,* 1995, 60, 6006–6007. Both of these disclosures pertain to the use of silane linkers in solid-supported organic synthesis which involve chemically distinct processes for attachment and cleavage of molecules to and from solid-supports from the instant invention which involves silyl ether linkers. Randolph, McClure and Danishefsky describe "Major simplifications in Oligosaccharide syntheses arising from a Solid-Phase Based Method: An Application to the Synthesis of Lewis b Antigen" in *The Journal of the American Chemical Society,* 1995, 117, 5712–5719. This disclosure involves the use of silicon bearing polymers to which sugar molecules are attached and cleaved via silicon-oxygen forming and breaking reactions which is also chemically distinct from the instant invention wherein molecules are attached to a solid support by silicon-oxygen bond formation and cleaved by silicon-carbon bond breaking. The methods above do not disclose the utility of aryl- and heteroaryl-silyl ethers in solid-supported organic synthesis nor do they teach a skilled practitioner of this art how to use said silyl ethers effectively therein.

SUMMARY OF INVENTION

Accordingly, the present invention is a process for preparing pharmaceuticals or agrochemicals comprising:

a) An aryllithium or heteroaryllithium reagent is first reacted with a dichlorosilane forming a silicon-carbon bond;
b) The resulting aryl-chlorosilane is reacted in one or more synthetic steps with a solid-supported hydroxyl group to form a silicon-oxygen bond (silyl ether) which thereby links the aromatic or heteroaromatic synthon to the solid support;
c) The solid-supported aromatic or heteroaromatic synthon is elaborated, in one or more synthetic steps, into solid-supported molecules which, when detached from the support, afford pharmaceuticals or agrochemicals.

DETAILED DESCRIPTION OF THE INVENTION

Specifically, the instant invention pertains to the use of silyl ethers in the attachment of molecules bearing aromatic and heteroaromatic rings to solid-supports for the purpose of engaging in solid-supported organic synthesis of libraries of small organic molecules. The use of silyl ethers in this fashion requires methods for forming silicon-carbon bonds between the aromatic or heteroaromatic ring and a dichlorosilane, methods for formation of a silicon-oxygen bond between the resulting aryl-chlorosilane and a solid-supported hydroxyl group, knowledge of the range of compatible solid-supports to which this hydroxyl group is attached, and methods for selective cleavage of a silicon-carbon bond that will liberate the desired product from the solid-support.

Throughout the detailed description and claims the following definitions will apply unless otherwise specified:

General Terms

| | |
|---|---|
| 1. Alkyl | A straight or branched chain of eight or fewer carbon atoms that is unsubstituted or substituted by one or two functional groups selected from the group consisting of: OH, NH$_2$, OCH$_3$, CO$_2$H, CO$_2$CH$_3$, CONH$_2$, $\overset{O}{\underset{\|}{C}}$, and CN. |
| 2. Lower Alkyl | A subset of alkyl which includes straight chain, branched or cyclic groups of 1–6 carbon atoms which lacks substitution by heteroatoms. |
| 3. Alkenyl | An alkyl group defined as above with one or two carbon double bonds. |
| 4. Aryl | A phenyl, a 1-naphthyl or a 2-naphthyl ring which is unsubstituted or substituted by 2–5 groups selected from the group consisting of: HO, H$_2$N, SH, F, Br, Cl, I, CH$_3$, CHO, CH$_2$OH, CO$_2$H, CN, CF$_3$, CCl$_3$, NO$_2$, phenyl, OR, NHR, NR$_2$, SR, C(=O)NHR, C(=O)OR, C(=O)R, SO$_2$NHR and SO$_2$R and suitably protected versions thereof wherein R is an alkyl or alkenyl group as described above. |
| 5. Heteroaryl | A 5- or 6-membered aromatic ring or a benzo-fused 5-or 6-membered aromatic ring system containing at least one N, O, or S atom which is unsubstituted or substituted by 2–5 groups selected from the group consisting of: HO, H$_2$N, SH, F, Br, Cl, I, CH$_3$, CHO, CH$_2$OH, CO$_2$H, CN, CF$_3$, CCl$_3$, NO$_2$, phenyl, OR, NHR, NR$_2$, SR, C(=O)NHR, C(=O)OR, C(=O)R, SO$_2$NHR and SO$_2$R and suitably protected versions thereof wherein R is an alkyl or alkenyl group as described above. |
| 6. Protecting Group | A chemical functionality that is temporarily installed to avoid an unwanted side reaction. Protection and deprotection strategies are well known to those skilled in the art of organic synthesis and are described in detail by Theodora W. Greene in Protective Groups in Organic Synthesis John Wiley and Sons, Inc, N.Y., N.Y. (1991). |
| 7. Chirality | Compounds of the invention contain one or more chiral centers. Structures and compound names lacking a specific stereochemical definition define all possible stereoisomers. |
| 8. Polar-Aprotic Solvent | A solvent selected from the group consisting of: DMF, DMA, NMP, MeCN, HMPA and DMSO as defined below. |

Reagents and solvents: Used herein, the following abbreviations have the following meanings: DMF refers to N,N-dimethylformamide, DCM refers to dichloromethane, THF refers to tetrahydofuran, Et$_2$O refers to diethyl ether, MeCN refers to acetonitrile, NMP refers to 1-N-methyl-2-pyrrolidinone, DMA refers to N,N-dimethylacetamde, DCC refers to 1,3-dicyclohexyldicarbodiimide, EDAC refers to 1-(3-dimethylaminopropyl)-3-ethylcarbodiimide, TBAF refers to tetrabutylammonium fluoride, MOM refers to methoxymethyl, TMEDA refers to N,N, N,N-tetramethylethylene diamine, TAS-F refers to tris (dimethylamino)sulfonium difluorotrimethylsilicate, Dess-Martin periodinane or Dess Martin reagent refers to 1,1,1-triacetoxy-1,1-dihydro-1,2-benziodoxol-3(1H)-one, DMAP refers to 4-N,N-dimethylaminopyridine, DMSO refers to dimethylsulfoxide, DBU refers to 1,8-Diazabicyclo[5.4.0]undec-7-ene, (i-Pr)$_2$NEt refers to N,N-diisopropylethylamine, LDA refers to lithium diisopropylamide, LiTMP refers to lithium 2,2,6,6-tetramethylpiperdinamide, n-BuLi refers to n-butyllithium, t-BuLi refers to tert-butyllithium, IBA refers to 1-hydroxy-1,2-benziodoxol-3(1H)-one 1-oxide, PDC refers to pyridinium dichromate, NaHMDS refers to sodium hexamethyldisilazide, LiHMDS refers to lithium hexamethyldisilazide, HMPA refers to hexamethylphosphoramide, TMS-Br refers to trimethylsilyl bromide, TFA refers to trifluoroacetic acid, MBHA refers to 4-methylbenzhydrylamine, BHA refers to benzhydrylamine and ZnCl$_2$ refers to zinc dichloride. CIMS refers to chemical ionization mass spectrometry, min is minutes, h is hours, rt is room temperature, and mL is milliliters.

Solid supports: Used herein the terms resin, resin bound, polymeric resin, polymeric resin support or polymeric support are to mean, at all occurrences, a bead or other solid support, which would be obvious to one of ordinary skill and knowledge in the art. The preferred polymer resins for use herein are the hydroxymethyl and Wang resins (available commercially from Nova Biochem). Other solid supports that are suitably substituted and made of a cross-linked polystyrene resin or polyethylene glycol-polystyrene resin can also be used. Additionally, a linker, defined here as any aliphatic or aromatic reagent which tethers the aryl silane to the solid-support and which lacks functionality that will participate in any synthetic chemistry subsequently carried out on the solid-support, can be used.

General Methods of Preparation

For all of the following Schemes, standard work-up and purification methods can be utilized and will be obvious to those skilled in the art. Synthetic methodologies that make up the invention are shown in Schemes I-V below. These Schemes are intended to describe the applicable chemistry through the use of specific examples and are not indicative of the scope of the invention.

In Scheme I treatment of MOM-protected aryl bromide 1 with n-butyllithium followed by quenching with dichlorodiisopropylsilane, at low temperature, provides the chlorodiisopropyl arylsilane 2. Alternatively, any bromo or iodobenzene derivative which is substituted by 2–5 groups selected from the group consisting of: HO, $H_2N$, SH, F, Br, Cl, $CH_3$, CHO, $CH_2OH$, $CO_2H$, CN, $CF_3$, $CCl_3$, $NO_2$, phenyl, OR, NHR, $NR_2$, SR, C(=O)NHR, C(=O)OR, C(=O)R, $SO_2NHR$, and $SO_2R$ or a suitably protected version thereof, wherein R is a straight or branched chain of eight or fewer carbon atoms that is unsubstituted or substituted by one or two functional groups selected from the group consisting of: OH, $NH_2$, $OCH_3$, $CO_2H$, $CO_2CH_3$, $CONH_2$, =O, and CN and may contain one or two carbon—carbon double bonds, can be reacted with n-butyllithim followed by quenching with any symmetrically or unsymmetrically dialkyl, of 1–8 carbons, but not limited to, substituted dichlorosilane. The resin-bound silyl ether is prepared by reacting the chlorodialkylarylsilane with hydroxymethyl resin (available from Bachem Calif., 1.00 meq/g) in the presence of an acid scavagner, such as imidazole, in DMF. Resin-bound silyl ethers analogous to 3 in Scheme I can be prepared from the properly substituted chloro or sulfonyl dialkylsilane and any solid-support containing a reactive hydroxyl functionality. The arylchlorosilane can also be first converted to an aryl-hydroxysilane and then activated by treatment with diethylazodicarboxylate and triphenylphosphine before reacting with a solid-supported hydroxyl group to generate a silyl-ether linkage. Preferably for the instant invention hydroxymethyl resin and Wang resin, however the following may also be used: a solid-supported hydroxyl group derived from $HO(CH_2)_nX(CH_2)_m$-polystyrene wherein: X is O, S, C(=O)NH, NHC(=O), N(Me)C(=O), C(=O)O, or OC(=O); n is an integer from 1 to 6 and m is zero or one, a solid-supported hydroxyl group derived from $HO(CH_2)_n$X-polyethyleneglycol-polystyrene composite polymer wherein: X is O, S, C(=O)NH, NHC(=O), N(Me)C(=O), C(=O)O, or OC(=O) and n is an integer from 1 to 6, a solid-supported hydroxyl group derived from $HO(CH_2)_nC(=O)$-MBHA resin or $HO(CH_2)_nC(=O)$-BHA resin and n is an integer from 1 to 6, a solid-supported hydroxyl group derived from (4-hydroxyphenyl)—$(CH_2)_pX(CH_2)_m$-polystyrene wherein: X is O, S, C(=O)NH, NHC(=O), N(Me)C(=O), C(=O)O, or OC(=O); p is an integer from 0 to 6 and m is zero or one or a solid-supported hydroxyl group derived from (4-hydroxyphenyl)-$(CH_2)_p$X-polyethyleneglycol-polystyrene composite polymer wherein: X is O, S, C(=O)NH, NHC(=O), N(Me)C(=O), C(=O)O, or OC(=O) and p is an integer from 0 to 6. The reaction is carried out in the presence of an acid scavanger (such as, but not limited to, imidazole, pyridine, 2,6-lutidine or DMAP) in an aprotic solvent (such as, but not limited to, DMF, DMA or DMSO).

Scheme I

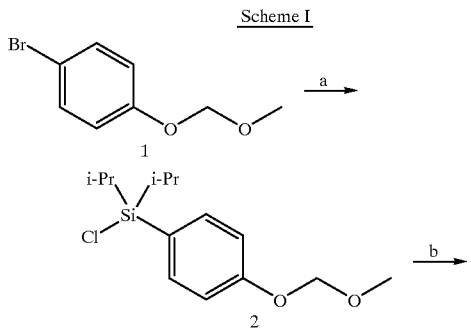

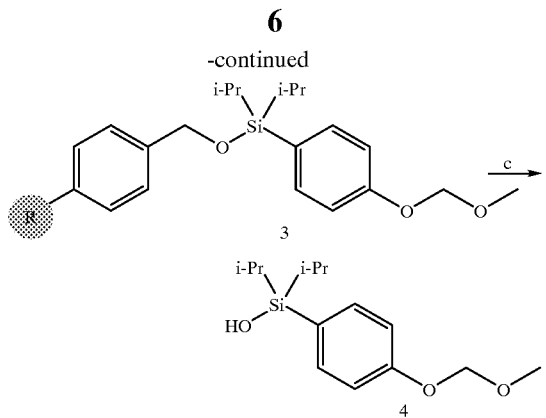

Scheme I. (a) n-BuLi, THF, -78° C. dichlorodiisopropylsilane: (b) DMF, imidazole, Hydroxymethylresin (1% crosslinked, Bachem California 1.00 meq/g: (c) TBAF, THF, rt.

Cleavage of the silicon-oxygen bond is illustrated in Scheme I. Treatment of resin-bound aryl silyl ether with tetrabutylammonium fluoride in THF at room temperature gives the silanol 4 as shown in Scheme I. The reaction can also be carried out using cesium fluoride in aqueous DMF.

It will be obvious to one skilled in the art, that derivatization of the resin-bound aryl silyl ethers is not limited to the chemical reactions shown in Schemes II-V and that other conventional chemistries can be applied to the intermediates disclosed herein. Scheme II depicts derivatization of resin-bound aryl silyl ether intermediate. Thus, treatment of resin-bound silyl ether 1 (3-Scheme I) with n-butyllithium in the presence of N,N,N',N'-tetramethylethylene diamine in diethyl ether followed by quenching with dry dimethylformamide gives the resin-bound silyl ether intermediate 2. Preparation of resin-bound intermediates similar to 2 in Scheme II can be formed from an appropriately substituted dialkyl aryl or heteroaryl silyl ether with a strong base (such as, but not limited to n-BuLi, t-BuLi, LDA, or LiTMP) and quenching with a suitably reactive reagent (such as, but not limited to, aldehydes, amides, acid chlorides, alkyl halides or carboxylic esters) in a suitable solvent (such as, but not limited to THF or diethyl ether).

Scheme II

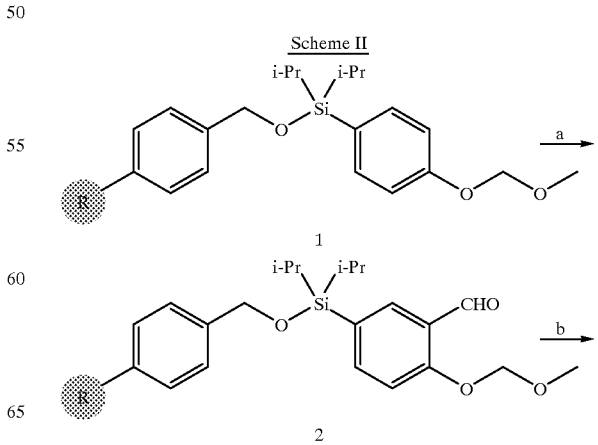

-continued

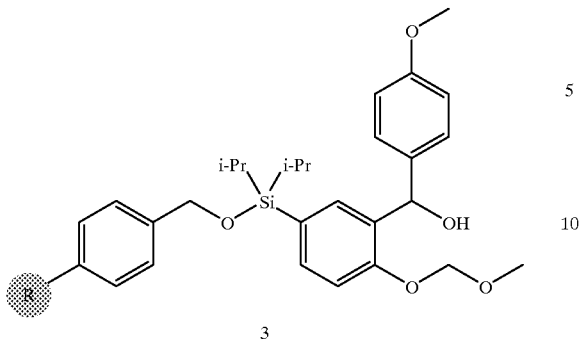

3

Scheme II. (a) 1. n-BuLi, TMEDA, Et₂O, 2. DMF: (b) n-BuLi, THF, p-bromoanisole.

-continued

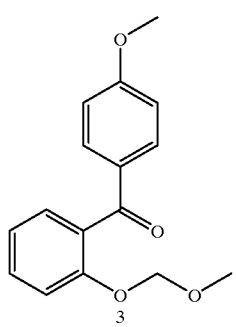

3

Scheme III. (a) Dess-Martin reagent, CH₂Cl₂, rt: (b) TBAF, DMF, 65° C.

Reaction of resin-bound silyl ether intermediate 2 in Scheme II with the aryllithium generated from para-methoxybromobenzene and n-butyllithium in THF, provides the resin-bound silyl ether intermediate alcohol 3. Again, it will be obvious to one skilled in the art, that analogues of 3 can be formed by reacting an alternative aryllithium or heteroaryllithium, generated from an arylbromide or properly substituted aromatic or heteroaromatic compound with a strong base (such as, but not limited to, n-BuLi, t-BuLi or LDA) in a suitable solvent (such as, but not limited to THF or diethyl ether).

Scheme III depicts oxidation of resin-bound silyl ether intermediate 1 (3-Scheme II) with Dess-Martin periodinane in dichloromethane to afford the resin-bound silyl ether intermediate 2. Oxidation of resin-bound intermediates is not limited to this reagent, but this transformation could also be carried by other oxidants (such as, but not limited to, PDC or IBA) in an appropriate solvent.

Scheme III illustrates cleavage of the carbon-silicon bond of the resin-bound silyl ether. Proto-ipsodesilylation of resin-bound silyl ether was carried out using tetrabutylammonium fluoride or TAS-F in DMF or another aprotic solvent or a mixture of aprotic solvents at 65° C.

Scheme IV depicts further derivatization of the resin-bound silyl ether intermediate 1 (2-Scheme III). Treatment of resin-bound silyl ether intermediate 1 (2-Scheme III) with 5% trifluoroacetic acid in dichloromethane results in selective cleavage of the MOM-protecting group. Alkylation of the resulting resin-bound phenol with 1-bromo-3,3-dimethyl-2-butanone in the presence of diisopropylethylamine and NMP at 80° C. provides resin-bound silyl ether intermediate 3.

Scheme III

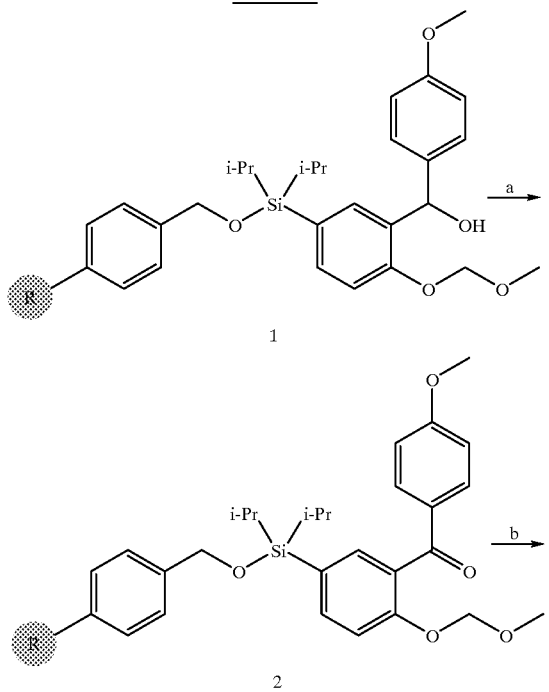

Scheme IV

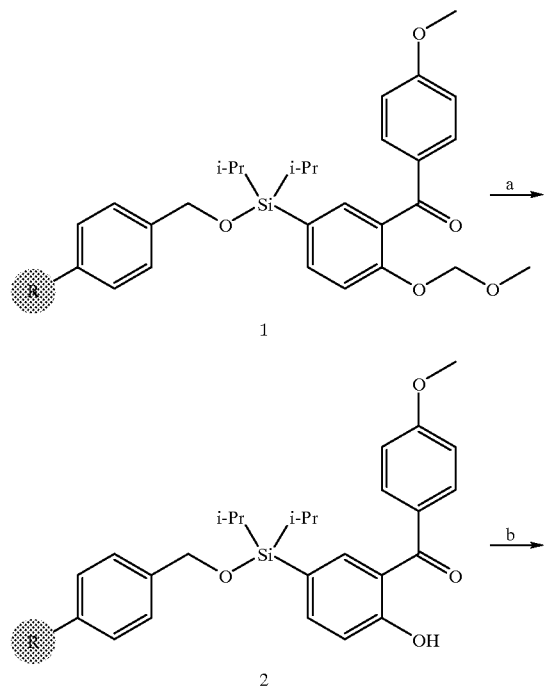

-continued

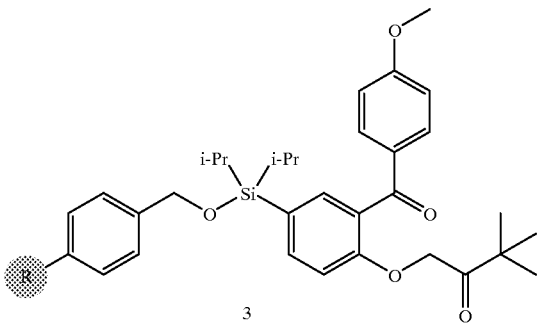

Scheme IV. (a) 5% TFA/CH$_2$Cl$_2$: (b) 1-bromo-3, 3-dimethyl-2-butanone, (i-Pr)$_2$NEt, NMP, 80° C.

Reaction of the resin-bound phenol can be carried out with other reactive species (such as, but not limited to, alkyl halides, alkyl sulfonates, acid chlorides or carboxylic esters) in the presence of a base (such as, but not limited to, Et$_3$N, or LiHMDS) in an aprotic solvent (such as, but not limited to DMF, THF, NMP or DMSO).

Scheme V depicts annulation of the resin-bound silyl ether 3 (1-Scheme V). Treatment of resin-bound silyl ether intermediate 1 with DBU in NMP gives the resin-bound benzofuran. A similar transformation could be carried out using an alternative base (such as, but not limited to, LiHMDS, LDA or LiTMP) in an appropriate solvent such as THF or diethyl ether.

The resin-bound benzofuran is finally cleaved from the resin using tetrabutylammonium fluoride or TAS-F in DMF or another polar-aprotic solvent at 65° C. Alternatively, the carbon-silicon bond could be cleaved using molecular bromine or iodine in dichloromethane or chloroform which would result in the formation of a carbon-halogen bond. The carbon-silicon bond could also be cleaved to form a carbon-oxygen bond by treatment of 2 in Scheme V with tetrabutylammonium fluoride and an oxidizing agent (such as, but not limited to, hydrogen peroxide or peracetic acid) or an electrophilic sulfur reagent (such as , but not limited to, dialkyldisulfide). And finally, the carbon-silicon bond could be cleaved to form a carbon—carbon bond by treatment with TAS-F in DMF or another polar-aprotic solvent followed by quenching with a reactive species (such as, but not limited to, alkyl halides of alkyl sulfonates).

The following nonlimiting examples illustrate the inventors' preferred methods for carrying out the process of the invention.

EXAMPLE 1

Preparation of Chlorodiisopropyl(4-methoxymethoxyphenyl)silane (2-Scheme I)

A solution of n-butyllithium (1.6M, 72.50 mL, 0.116 mol) was added slowly dropwise to a solution of bromo-4-methoxymethoxybenzene (25.23 g, 0.116 mol) in dry THF (110 mL) at −78° C. After stirring for 50 min at −78° C., dichlorodiisopropylsilane (21.00 mL, 0.116 mol) was charged into the flask. The reaction mixture was slowly allowed to warm to room temperature with stirring. Diethyl ether (100 mL) was added, the mixture was then stirred for 15 min and filtered. The filtrate was concentrated in vacuo to an oil. The oil was purified by short path distillation (116–128° C./ 0.18 mm Hg) to afford the compound (23.7 g, 71%) as a slightly cloudy pale yellow oil.

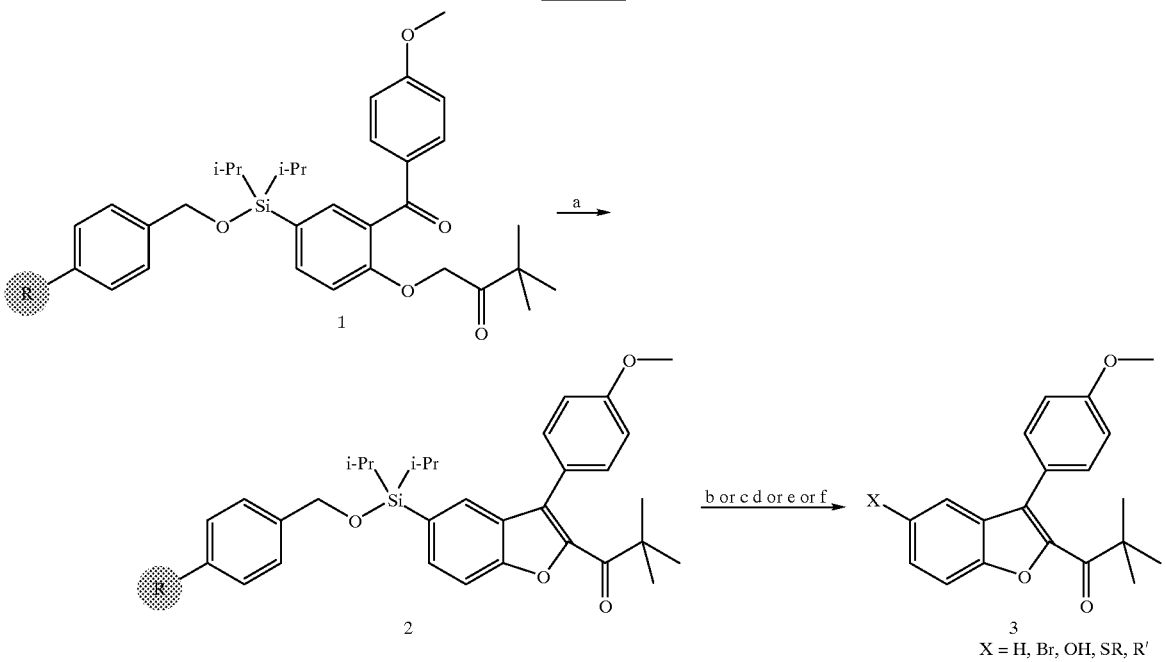

Scheme V. DBU, NMP, 80° C.; (b) TBAF, DMF, 65° C.: X = H; (c) Br$_2$, CH$_2$Cl$_2$: X = Br; (d) TBAF, H$_2$O: X = OH; (e) TAS-F, DMF, RSSR: X = SR; (f) TAS-F, DMF, R'Y: X = R'

$^1$H nuclear magnetic resonance spectroscopy (NMR) (400 MHz, CDCl$_3$) δ 7.52 (d, J=8.7 Hz, 2 H), 7.06 (d, J=8.7 Hz, 2 H), 5.20 (s, 2 H), 3.49 (s, 3 H), 1.42–1.35 (m, 2 H), 1.08 (d, J=7.5 Hz, 6 H), 1.00 (d, J=7.5 Hz, 6 H); $^{13}$C NMR (400

MHz, CDCl$_3$) δ 158.80, 135.90, 124.39, 115.65, 94.12, 56.16, 17.00, 16.78, 13.85; chemical ionization mass spectroscopy (CIMS) m/z 286, 255, 251, 243, 151.

EXAMPLE 2
Preparation of resin-bound aryl silyl ether intermediate (3-Scheme I)

To a suspension of hydroxymethyl resin (Bachem California, 1.0 meq/g) and imidazole (1.50 g, 22.04 mmol) in DMF (40 mL) was added chlorodiisopropyl(4-methoxymethoxyphenyl)silane (4.04 g, 14.08 mmol). The resulting mixture was agitated at room temperature for 43 h. The resin was collected by filtration and washed with DMF, THF and finally dichloromethane. The product was dried in vacuo to give the resin (6.92 g) as an off-white solid.

$^{13}$C NMR (400 MHz, CDCl$_3$) δ 94.2, 56.0, 17.6, 17.5, 12.3; infrared spectroscopy (IR) (KBr) 1236, 1153, 1077, 755 cm$^{-1}$ (Si—OR stretch).

EXAMPLE 3
Reaction of resin-bound aryl silyl ether intermediate 3-Scheme I with TBAF To a suspension of resin-bound aryl silyl ether 3-Scheme I (0.249 g) in THF (3 mL) was added tetrabutylammonium fluoride (1.0M in THF, 1.00 mL, 1.00 mmol). The mixture was agitated at room temperature for 24 h. The resin was filtered and then washed with THF (5×6 mL). The filtrate was concentrated in vacuo and then dissolved in ethyl acetate. The solution was washed with water, brine, dried (Na$_2$SO$_4$), filtered and concentrated in vacuo to give diisopropyl(4-methoxymethoxyphenyl)silanol (0.048 g) as a pale yellow oil.

$^1$H NMR (400 MHz, CDCl$_3$) δ 7.44 (d, J=8.5 Hz, 2 H), 7.00 (d, J=8.5 Hz, 2 H), 5.16 (s, 2 H), 3.45 (s, 3 H), 1.61 (br s, 1 H), 1.21–1.10 (m, 2 H), 1.00 (d, J=7.3 Hz, 6 H), 0.93 (d, J=7.3 Hz, 6 H); CIMS m/z 269, 268, 251, 237, 225, 197, 151, 107.

EXAMPLE 4
Preparation of resin-bound aryl silyl ether intermediate 2-Scheme II To an ice-cold suspension of resin-bound intermediate 1-Scheme II (0.500 g) in diethyl ether (5 mL) and N,N,N',N'-tetramethylethylene diamine (0.172 mL, 1.14 mmol) was added n-butyllithium (1.6M, 0.625 mL, 1.00 mmol) in small portions (ca. 0.20 mL) over a 10 min period. The resulting suspension was agitated at 0° C. for 1 h. Dry DMF (0.310 mL, 4.00 mmol) was charged into the flask and the reaction mixture was agitated at 0° C. for 30 min and then at room temperature for 30 min. Aqueous saturated NH$_4$Cl (5 mL) was added and the reaction mixture was stirred at room temperature for 10 min. The resin was filtered and washed with diethyl ether, water, diethyl ether and dichloromethane. The product was dried in vacuo overnight to yield the title resin (0.471 g) as a yellow solid.

13 C NMR (400 MHz, CDCl$_3$) δ 189.8, 94.5, 56.5, 17.5, 12.2; IR (KBr) 1681 cm$^{-1}$ (carbonyl stretch).

EXAMPLE 5
Preparation of resin-bound aryl silyl ether intermediate 3-Scheme II.

To a solution of 4-methoxybromobenzene (0.374 g, 2.00 mmol) in THF (10 mL) at −78° C. was slowly added n-butyllithium (1.6M, 1.25 mL, 2.00 mmol). The resulting mixture as stirred at −78° C. for 30 min and then added via cannula to a suspension of resin-bound aryl silyl ether intermediate 2-Scheme II, precooled to 0° C. The mixture was agitated at 0° C. for 1 h then the ice-bath was removed and the suspension was agitated for an additional 3 h. Aqueous saturated NH$_4$Cl (20 mL) was added to the reaction and the suspension was agitated for 30 min. The resin was filtered and washed with water, diethyl ether, THF and dichloromethane. The product was dried in vacuo to give resin-bound silyl ether intermediate 3-Scheme II. (0.491 g) as a cream colored solid.

$^{13}$C NMR (400 MHz, CDCl$_3$) δ 94.0, 72.1, 56.1, 55.2, 17.6, 17.5, 12.3.

EXAMPLE 6
Preparation of resin-bound aryl silyl ether intermediate 2-Scheme III.

To a suspension of resin-bound aryl silyl ether intermediate 1-Scheme III (0.276 g) in dichloromethane (3.5 mL) was added a suspension of 1,1,1-triacetoxy-1,1-dihydro-1,2-benziodoxol-3(1H)-one (2.56 g, 0.604 mmol) in methylene chloride (6 mL). The mixture was agitated at room temperature for 4.5 h. Ice-cold NaOH (1 M, 20 mL) was added and the reaction mixture was agitated for 10 min. The resin was filtered and washed with NaOH (1M), water, methanol, dioxane, THF, diethyl ether and dichloromethane. The product was dried in vacuo to give the title resin (0.247 g) as a mustard colored solid.

$^{13}$C NMR (400 MHz, CDCl$_3$) δ 94.4, 56.3, 55.4, 17.4, 12.2; IR (KBr) 1662 cm$^{-1}$ (carbonyl stretch).

EXAMPLE 7
Cleavage of benzophenone 2-Scheme III with TBAF in DMF

To a suspension of resin-bound aryl silyl ether intermediate 2-Scheme III (0.124 g) in DMF (1 mL) was added tetrabutylammonium fluoride (1.0M in THF, 0.500 mL, 0.500 mmol). The mixture was agitated for 8 h at 65° C. After cooling to room temperature, the resin was removed by filtration, washing with diethyl ether (3×10 mL), water (10 mL) and THF (10 mL). The aqueous layer was removed and the organic layer was washed with water, brine, dried (Na$_2$SO$_4$), filtered and concentrated in vacuo. The residue was taken up in chloroform, filtered through a plug of basic aluminum oxide and concentrated in vacuo to give 4-methoxy-2'-methoxymethoxybenzophenone (0.006 g) as a cloudy oil.

$^1$H NMR (400 MHz, CDCl$_3$) δ 7.75 (d, J=9.0 Hz, 2 H), 7.36 (t, J=8.3 Hz, 1 H), 7.25 (d, J=7.6 Hz, 1 H), 7.14 (d, J=8.3 Hz, 1 H), 7.02 (t, J=8.3 Hz, 1 H), 6.84 (d, J=9.0 Hz, 2 H), 5.01 (s, 2 H), 3.80 (s, 3 H), 3.26 (s, 3 H).

EXAMPLE 8
Preparation of resin-bound aryl silane intermediate 2-Scheme IV

To an ice-cold suspension of resin-bound aryl silyl ether intermediate 1-Scheme IV (0.118 g) in dichloromethane (2 mL) was added trifluoroacetic acid (0.1 mL). The suspension was agitated at 0° C. for 1.5 h. The resin was filtered and washed with dichloromethane. The product was dried in vacuo to give the title resin (0.126 g) as a yellow/lime colored solid.

$^{13}$C NMR (400 MHz, CDCl$_3$) δ 55.8, 17.4, 12.1; IR (KBr) 1621 cm$^{-1}$ (carbonyl stretch).

EXAMPLE 9
Preparation of resin-bound aryl silyl ether intermediate 3-Scheme IV.

To a suspension of phenol resin 2-Scheme IV (0.250 g) in NMP (2 mL) was added N,N-diisopropylethylamine (0.523 mL, 3.00 mmol) and 1-bromo-3,3-dimethyl-2-butanone (0.336 mL, 2.50 mmol). The mixture was heated to 80° C.

for 2 h, with agitation. The resin was allowed to cool to room temperature, then filtered and washed with NMP and dichloromethane. The product was dried in vacuo to give the title resin (0.243 g) as a pale orange solid.

$^{13}$C NMR (400 MHz, CDCl$_3$) δ 194.8, 82.3, 66.1, 55.4, 28.0, 17.4, 12.2; IR (KBr) 1726, 1660 cm$^{-1}$ (carbonyl stretch).

EXAMPLE 10

Preparation of resin-bound aryl silane intermediate 2-Scheme V.

To a suspension of resin-bound aryl silyl ether intermediate 1-Scheme V (0.136 g) in NMP (1.5 mL) was added 1,8-diazabicyclo[5.4.0]undec-7-ene (0.224 mL, 1.50 mmol). The mixture was heated to 80° C. for 1 h, with agitation. After cooling to room temperature the resin was filtered and washed with NMP and dichloromethane. The product was dried in vacuo to give the title resin (0.123 g ) as a pink orange solid.

$^{13}$C NMR (400 MHz, CDCl$_3$) δ 55.2, 44.3, 26.6, 17.5, 12.3; IR (KBr) 1673 cm$^{-1}$ (carbonyl stretch).

EXAMPLE 11

Treatment of resin-bound aryl silyl ether 2-Scheme V with TBAF.

A suspension of resin-bound intermediate 2-Scheme V (0.209 g) in DMF (2 mL) was treated with tetrabutylammonium fluoride (1M in THF, 1.00 mL, 1.00 mmol) and the mixture was heated to 65° C. with agitation, for 1 h. The mixture was allowed to cool to room temperature and water (10 mL) was added. The mixture was filtered washing with diethyl ether (3×10 mL). The filtrate was transferred to a separatory funnel, the aqueous layer was removed and the organic layer was washed with water, brine, dried (Na$_2$SO$_4$), filtered and concentrated in vacuo. The residue was taken up in chloroform and filtered through a plug of basic aluminum oxide. The filtrate was concentrated in vacuo and then this process was repeated a second time to give the benzofuran 3-Scheme V (R=H) (0.024 g) as a pale cloudy yellow oil.

$^1$H NMR (400 MHz, CDCl$_3$) δ 7.55–7.41 (m, 5 H), 7.23 (m, 1 H), 6.95 (d, J=8.8 Hz, 2 H), 3.81 (s, 3 H), 1.35 (s, 9 H); CIMS (M+H) 309.

What is claimed is:

1. A process for preparing pharmaceuticals or agrochemicals comprising:
   a) An aryllithium or heteroaryllithium reagent is first reacted with a substituted or unsubstituted dichlorosilane forming a silicon-carbon bond;
   b) The resulting aryl-chlorosilane is reacted in one or more synthetic steps with a solid-supported hydroxyl group to form a silicon-oxygen bond (silyl ether) which thereby links the aromatic or heteroaromatic synthon to the solid support;
   c) The solid-supported aromatic or heteroaromatic synthon is reacted, in one or more synthetic steps, to form a solid-supported molecules which, when detached from the support, afford pharmaceuticals or agrochemicals.

2. A process according to claim 1 wherein the dichlorosilane is symmetrically substituted by two identical lower alkyl groups of 1–6 carbon atoms which are straight chain, branched or cyclic.

3. A process according to claim 1 wherein the dichlorosilane is unsymmetrically substituted by a phenyl ring and an alkyl group or by two different lower alkyl groups of 1 to 6 carbon atoms which are straight chain, branched or cyclic.

4. A process according to claim 1 wherein the aryllithium is a phenyl, a 1-naphthyl or a 2-naphthyl ring which is unsubstituted or substituted by 2–5 groups selected from the group consisting of: HO, H$_2$N, SH, F, Br, Cl, CH$_3$, CHO, CH$_2$OH, CO$_2$H, CN, CF$_3$, CCl$_3$, NO$_2$, phenyl, OR, NHR, NR$_2$, SR, C(=O)NHR, C(=O)OR, C(=O)R, SO$_2$NHR, and SO$_2$R or a suitably protected version thereof, wherein R is a straight or branched chain of eight or fewer carbon atoms that is unsubstituted or substituted by one or two functional groups selected from the group consisting of: OH, NH$_2$, OCH$_3$, CO$_2$H, CO$_2$CH$_3$, CONH$_2$,

and CN and may contain one or two carbon—carbon double bonds.

5. A process according to claim 1 wherein the heteroaryllithium is a 5- or 6-membered aromatic ring or a benzofused 5- or 6-membered aromatic ring system containing at least one N, O, or S atom which is unsubstituted or substituted by 2–5 groups selected from the group consisting of: HO, H$_2$N, SH, F, Br, Cl, CH$_3$, CHO, CH$_2$OH, CO$_2$H, CN, CF$_3$, CCl$_3$, NO$_2$, phenyl, OR, NHR, NR$_2$, SR, C(=O)NHR, C(=O)OR, C(=O)R, SO$_2$NHR, and SO$_2$R or a suitably protected version thereof, wherein R is a straight or branched chain of eight or fewer carbon atoms that is unsubstituted or substituted by one or two functional groups selected from the group consisting of: OH, NH$_2$, OCH$_3$, CO$_2$H, CO$_2$CH$_3$, CONH$_2$,

and CN and may contain one or two carbon—carbon double bonds.

6. A process according to claim 1 wherein the aryl-chlorosilane is reacted in one step by treatment with a base and a solid-supported hydroxyl group to generate a silyl-ether linkage.

7. A process according to claim 1 wherein the aryl-chlorosilane is first converted to an aryl-hydroxysilane and then activated by treatment with diethylazodicarboxylate and triphenylphosphine before reacting with a solid-supported hydroxyl group to generate a silyl-ether linkage.

8. A process according to claim 1 wherein the aryl-chlorosilane is first converted to an aryl-triflate and then reacted with a base and a solid-supported hydroxyl group to generate a silyl-ether linkage.

9. A process according to claim 1 wherein the solid-supported hydroxyl group is a hydroxyl group of hydroxymethyl polystyrene, p-benzyloxybenzyl alcohol resin, ethyleneglycol 2-chlorotrityl resin, 4-hydroxymethylbenzoic acid BHA resin, 4-hydroxymethylbenzoic acid MBHA resin or polyethyleneglycol-polystyrene composite polymer.

10. A process according to claim 1 wherein the solid-supported hydroxylgroup is a hydroxyl group of HO(CH$_2$)$_n$X(CH$_2$)$_m$-polystyrene wherein: X is O, S, C(=O) NH, NHC(=O), N(Me)C(=O), C(=O)O, or OC(=O); n is an integer from 1 to 6 and m is zero or one.

11. A process according to claim 1 wherein the solid-supported hydroxylgroup is a hydroxyl group of HO(CH$_2$)$_n$X-polyethyleneglycol-polystyrene composite polymer wherein: X is O, S, C(=O)NH, NHC(=)O, N(Me) C(=O), C(=O)O, or OC(=O) and n is an integer from 1 to 6.

12. A process according to claim 1 wherein the solid-supported hydroxylgroup is a hydroxyl group of HO(CH$_2$)$_n$C(=O)—MBHA resin or HO(CH$_2$)$_n$C(=O)—BHA resin and n is an integer from 1 to 6.

13. A process according to claim 1 wherein the solid-supported hydroxylgroup is a hydroxyl group of (4-hydroxyphenyl)—(CH$_2$)$_p$X(CH$_2$)$_m$-polystyrene wherein: X is O, S, C(=O)NH, NHC(=)O, N(Me)C(=O), C(=O)O, or OC(=O); p is an integer from 0 to 6 and m is zero or one.

14. A process according to claim 1 wherein the solid-supported hydroxylgroup is a hydroxyl group of (4-hydroxyphenyl)—(CH$_2$ )$_p$X-polyethyleneglycol-polystyrene composite polymer wherein: X is O, S, C(=O)NH, NHC(=)O, N(Me)C(=O), C(=O)O, or OC(=O) and p is an integer from 0 to 6.

15. A process according to claim 1 wherein the carbon-silicon bond attaching the pharmaceutical or agrochemical to the solid support is cleaved by treatment with tetrabutylammonium fluoride or tris (dimethylamino) sulfonium difluorotrimethylsilicate in a polar-aprotic solvent or a mixture of polar-aprotic solvents at a temperature above 45° C.

16. A process according to claim 1 wherein the silicon-oxygen bond attaching the pharmaceutical or agrochemical to the solid support is cleaved by treatment with tetrabutylammonium fluoride in tetrahydrofuran, cesium fluoride in N,N-dimethylformamide, or trifluoroacetic acid in dichloromethane at less than 45° C.

17. A process according to claim 1 wherein the silicon-oxygen bond attaching the pharmaceutical or agrochemical to the solid-support is first cleaved according to claim 16 and then the silicon-carbon bond of the resulting silanol is cleaved by treatment with tetrabutylammonium fluoride or tris(dimethylamino)sulfonium difluorotrimethylsilicate in a polar-aprotic solvent or a mixture of polar-aprotic solvents at a temperature above 45° C.

18. A process according to claim 1 wherein the silicon-carbon bond attaching the pharmaceutical or agrochemical to the solid support is converted to an oxygen-carbon bond in one or more steps by treatment with tetrabutylammonium fluoride and an oxidizing agent.

19. A process according to claim 1 wherein the silicon-carbon bond attaching the pharmaceutical or agrochemical to the solid support is converted to an carbon—carbon bond by treatment with tris(dimethylamino)sulfonium (trimethylsilyl)difluoride and an electrophilic carbon source.

20. A process according to claim 1 wherein the silicon-carbon bond attaching the pharmaceutical or agrochemical to the solid support is converted to an sulfur-carbon bond by treatment with tris(dimethylamino)sulfonium (trimethylsilyl)difluoride and an electrophilic sulfur source.

21. A process according to claim 1 wherein the silicon-carbon bond attaching the pharmaceutical or agrochemical to the solid support is converted to an halogen-carbon bond by treatment with tris(dimethylamino)sulfonium (trimethylsilyl)difluoride and an electrophilic halogen source.

22. A process according to claim 1 wherein a library of greater than twenty pharmaceuticals or agrochemicals bearing aromatic or heteroaromatic moieties are prepared via automated synthesis.

23. A process according to claim 1 wherein a library of greater than twenty pharmaceuticals or agrochemicals bearing aromatic or heteroaromatic moieties are prepared via manual synthesis.

24. A process according to claim 18 wherein the oxidizing agent is hydrogen peroxide, or peracetic acid.

25. A process according to claim 19 wherein the electrophilic carbon source is an aldehyde, an acid chloride, an alkyl halide, or an alkyl sulfonate.

26. A process according to claim 20 wherein the electrophilic sulfur source is a disulfide, a sulfinyl halide, a sulfonyl chloride, or an thiosulfonate.

27. A process according to claim 21 wherein the electrophilic halogen source is I$_2$, Br$_2$, Cl$_2$, Icl, or tris (dimethylamino)sulfonium difluorotrimethylsilicate and N-halosuccinimides in DMF or another polar-aprotic solvent.

* * * * *

UNITED STATES PATENT AND TRADEMARK OFFICE
CERTIFICATE OF CORRECTION

PATENT NO. : 6,180,718 B1
DATED : January 30, 2001
INVENTOR(S) : Boehm et al.

It is certified that error appears in the above-identified patent and that said Letters Patent is hereby corrected as shown below:

Column 6,
Lines 7, 57 and 64, "R" (shaded) should read -- P -- (shaded)

Column 7,
Lines 14, 51 and 65, "R" (shaded) should read -- P -- (shaded)

Column 8,
Lines 51 (2 times) and 65, "R" (shaded) should read -- P -- (shaded)

Column 9,
Lines 13, 45 and 55, "R" (shaded) should read -- P -- (shaded)

Column 10,
Line 50, "b or c d or e or f" should read -- b or c or d or e or f --

Signed and Sealed this

Thirtieth Day of July, 2002

Attest:

Attesting Officer

JAMES E. ROGAN
Director of the United States Patent and Trademark Office